United States Patent [19]

Sickler, Jr.

[11] Patent Number: 5,597,580
[45] Date of Patent: Jan. 28, 1997

[54] METHOD AND APPARATUS FOR IMPROVING THE APPEARANCE OF SPIDER VEINS

[76] Inventor: Ernest H. Sickler, Jr., Elizabeth, N.J.

[21] Appl. No.: 237,219

[22] Filed: May 3, 1994

[51] Int. Cl.$^6$ .................................................. A61F 13/00
[52] U.S. Cl. ......................... 424/443; 424/445; 424/446; 424/195.1
[58] Field of Search ................................... 424/447, 443, 424/445, 446, 195.1

[56] References Cited

U.S. PATENT DOCUMENTS

| | | | |
|---|---|---|---|
| 4,153,153 | 5/1979 | Herzog | 206/0.5 |
| 4,318,906 | 3/1992 | Llopart | 424/195 |
| 4,814,171 | 3/1989 | Marty | 424/95 |
| 4,933,177 | 6/1990 | Grollier | 424/74 |
| 5,080,901 | 1/1992 | Hangay | 424/195.1 |
| 5,268,176 | 12/1993 | Znaiden | 424/401 |

OTHER PUBLICATIONS

D. Tkac, ed., *The Doctors Book of Home Remedies,* Rodale Press: Emmaus, Pa., 1990, pp. 86, 616–20.
*The Vitamin and Herb Guide,* Global Health Ltd.: Tofield, Alberta, Canada, 1992, pp. 34–35, 55–57.
H. Ellis, *Varicose Veins,* Arco Publishing, Inc.: New York, 1983, pp. 93–94.
H. C. Baron, *Varicose Veins,* William Morrow and Company, Inc.: New York, 1979, p. 126.
W. H. Hylton, ed., *The Rodale Herb Book,* Rodale Press: Emmaus, Pa., 1974, pp. 74, 77–78.
*Examiner,* Nov. 30, 1993, p. 4.

Primary Examiner—D. Gabrielle Phelan
Attorney, Agent, or Firm—Claire Ann Koegler

[57] ABSTRACT

A method and article are disclosed for topical application of tea, such as orange pekoe or black, to improve the appearance of spider veins and varicose veins. A method and article are also disclosed for topical application of tea to improve circulation in the extremities.

6 Claims, 2 Drawing Sheets

5,597,580

METHOD AND APPARATUS FOR IMPROVING THE APPEARANCE OF SPIDER VEINS

BACKGROUND OF THE INVENTION

This invention relates to the non-invasive treatment of spider veins and varicose veins. Varicose veins are weakened veins in which blood collects leading to a swollen and bluish appearance of the veins. They occur most commonly in the legs. Primary varicose veins are believed to be hereditary, whereas secondary varicose veins may occur as a result of an injury. Spider veins are small venules in the skin usually having a reddish appearance, most commonly found in women, and believed to be hormonal. They too occur most commonly in the legs.

Traditionally, varicose veins have been treated by surgery or injection treatments. Preventive tips include keeping one's weight down, raising the legs, wearing support hose, and not smoking. D. Tkac, ed., *The Doctors Book of Home Remedies,* Rodale Press: Emmaus, Pa., 1990, pp. 616–20. Other recommendations include ingesting B complex, C, and E vitamins and herbs such as butchers broom, hawthorn, horsechestnut, marigold, misletoe, witch hazel, white oak bark and yarrow. *The Vitamin & Herb Guide,* Global Health Ltd.: Tofield, Alberta, Canada, 1992, pp. 34–35. More recently, it has been suggested that a substance called anthocyanosides in bilberries can be ingested to erase varicose veins. *Examiner,* Nov. 30, 1993, p. 4.

Spider veins have also been treated by injection treatments, heat, and electrolysis. H. Ellis, *Varicose Veins,* Arco Publishing, Inc.: New York, 1983, p. 94. In the case of spider veins, such treatment may result in dicoloration of the skin. H. Ellis, *Varicose Veins,* at p. 94; H. C. Baron, *Varicose Veins,* William Morrow and Company, Inc.: New York, 1979, p. 126. Some authorities recommend not treating spider veins but rather covering them cosmetically. H. Ellis, *Varicose Veins,* at p. 94; H.C. Baron, *Varicose Veins,* at p. 126.

SUMMARY OF THE INVENTION

One object of this invention is to improve the appearance of spider veins. Another object is to remove spider veins. A further object of this invention is to improve the appearance of varicose veins. A still further object of this invention is to remove varicose veins. Yet another object of this invention is to improve circulation in the extremities.

DETAILED DESCRIPTION OF THE INVENTION

Figure 1A:
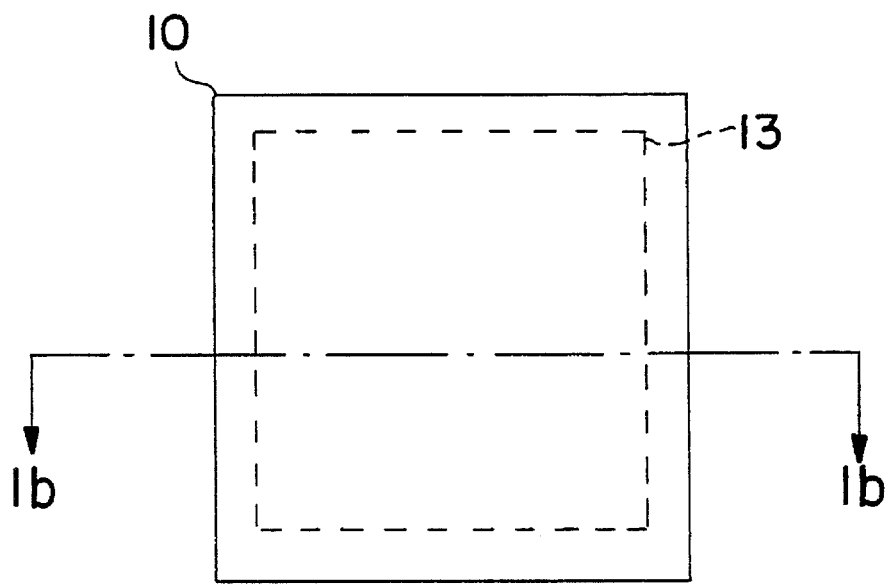
FIG. 1a shows a top view of an cloth pad containing tea for use in the practice of the invention.
Figure 1B:
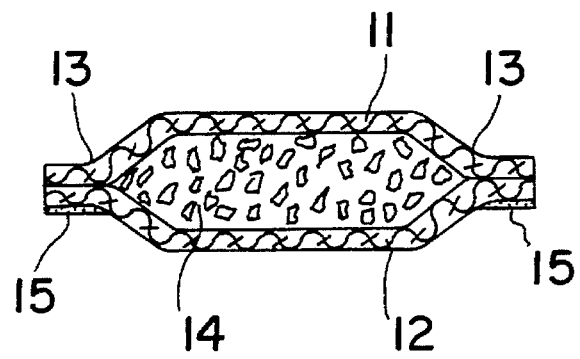
FIG. 1b shows a cross-section view of the same cloth pad.

It has been found that tea, such as orange pekoe or black, consisting of tannin, caffeine, and essential oils, applied topically (not ingested) improves the appearance of, and may be said to remove, spider veins and varicose veins. The tea is conveniently enclosed in a cloth pad 10 measuring approximately 3 inches by 3 inches, as is illustrated in FIG. 1a. As shown in FIG. 1b, the pad 10 has an outer layer or top portion 11 and an inner layer or bottom portion 12, which are attached, by stitching, glue, or other appropriate means, at seams 13 to create a pouch-like region. Loose tea 14 is contained in the pouch-like region. An effective amount of tea is approximately 0.1 to 0.2 ounces. Adhesive 15 may optionally be provided on the inner layer or bottom portion 12 adjacent the seams 13.

For best results, the extremity being treated should be at a level lower than the heart to facilitate an unimpeded flow of blood to the area being treated. The tea may simply be held in place on the area being treated. Preferably, the tea-containing cloth pad 10 is applied to the area being treated by alternately patting and rubbing gently. During the rubbing step, the rubbing should proceed from the area being treated toward a nearby fatty portion (as distinguished from bony portion) of the extremity. More preferably, the alternate patting and rubbing should continue for approximately 15 to 30 minutes. Optionally, the pad 10 may be soaked in water prior to being applied to the area being treated.

The veins being treated should fade gradually, changing from purple to deep red to lighter red to a more normal skin color. Improvement in the appearance of the affected area may be noticeable after one such treatment. This treatment may be repeated each day for up to a week. Spider veins may reappear when the extremity is exposed to cold temperatures. In this case, the treatment may be repeated.

Figure 2:
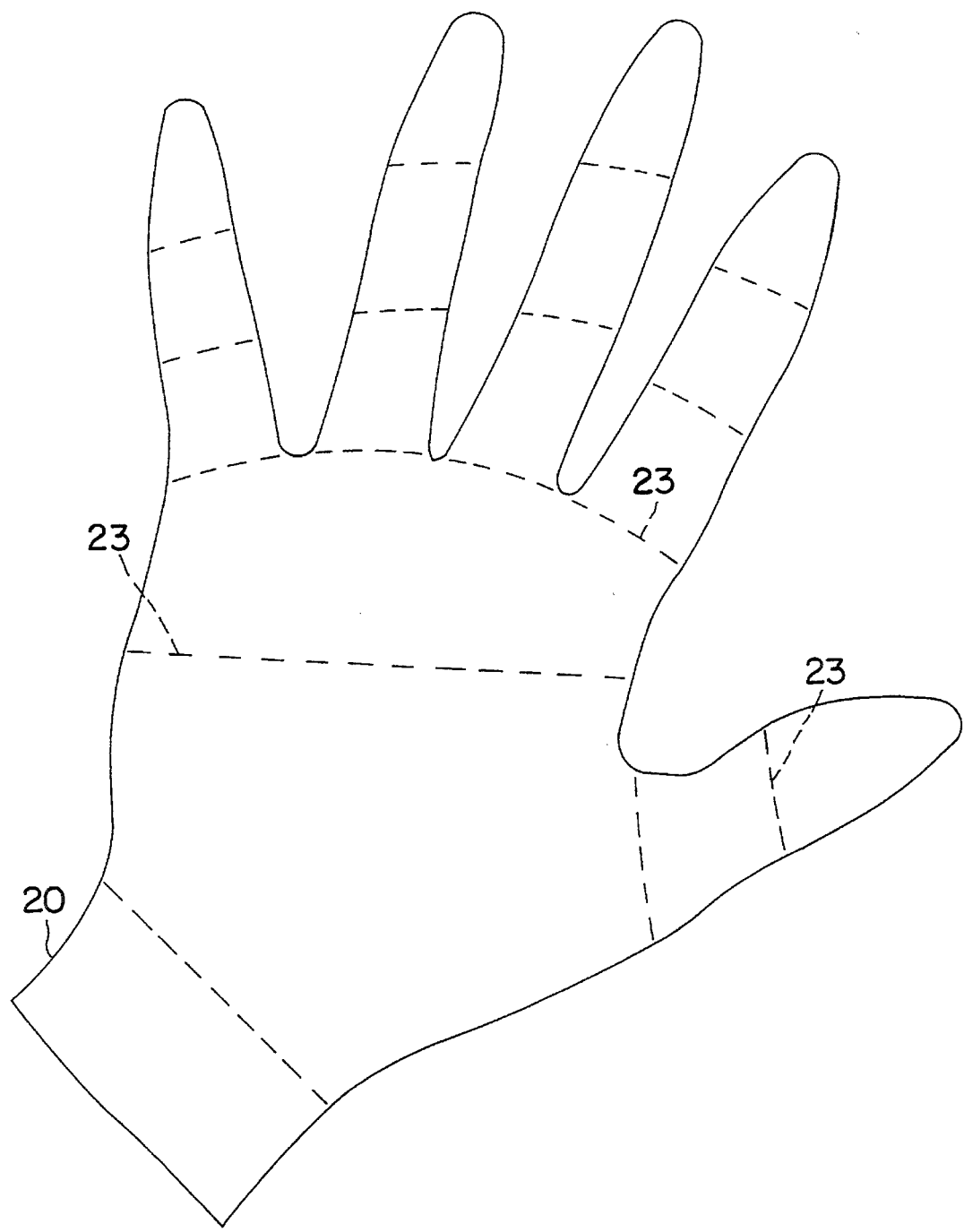
FIG. 2 shows a palm view of a glove containing tea for use in the practice of the invention.

Topical application of tea has also been found to improve circulation in the extremities. For example, tea may be rubbed on the hands or feet for several minutes following exposure to cold. Alternatively, the tea may be contained in an article of clothing, such as a glove, mitten, muff, sock, stocking, or leg warmer, which may then be placed on the extremity to be treated. As shown in FIG. 2, for example, a glove 20 may be constructed by joining along one or more seams 23 a first, outer layer with a second, inner layer (not shown) in the same form as, but smaller in size than, the first, outer layer, whereby the tea is contained in one or more pouch-like regions between the outer layer and the inner layer.

It is understood that the above-described arrangements are merely illustrative of the many possible specific embodiments which represent applications of the present invention. Numerous and varied other arrangements can readily be devised in accordance with the principles of the present invention without departing from the spirit and scope thereof.

What is claimed is:

1. A method for improving the appearance of spider veins in human extremities comprising the steps of:

lowering relative to the heart the area of the extremity to be treated; and applying topically to the area of the extremity to be treated an effective amount of loose tea contained in a pouch, said tea consisting essentially of tannin, caffeine, and essential oils;

wherein the step of applying tea is practiced by alternately patting and rubbing the area of the extremity to be treated for about 15 to 30 minutes and the step of rubbing the area to be treated is practiced by rubbing the tea from the area of the extremity to be treated toward a nearby fatty portion.

2. A method in accordance with claim 1 wherein the pouch contains approximately 0.1 to 0.2 ounces of loose tea.

3. A method for improving circulation in human hands and feet comprising the steps of:

lowering relative to the heart the area of the extremity to be treated; and applying topically to the area of the extremity to be treated an effective amount of loose tea contained in a pouch, said tea consisting essentially of tannin, caffeine, and essential oils;

wherein the step of applying tea is practiced by alternately patting and rubbing the area of the extremity to be treated for about 15 to 30 minutes and the step of rubbing the area to be treated is practiced by rubbing the tea from the area of the extremity to be treated toward a nearby fatty portion.

4. A method in accordance with claim 3 wherein the pouch contains approximately 0.1 to 0.2 ounces of loose tea.

5. A method for improving the appearance of varicose veins in human extremities comprising the steps of:

lowering relative to the heart the area of the extremity to be treated; and applying topically to the area of the extremity to be treated an effective amount of loose tea contained in a pouch, said tea consisting essentially of tannin, caffeine, and essential oils;

wherein the step of applying tea is practiced by alternately patting and rubbing the area of the extremity to be treated for about 15 to 30 minutes and the step of rubbing the area to be treated is practiced by rubbing the tea from the area of the extremity to be treated toward a nearby fatty portion.

6. A method in accordance with claim 5 wherein the pouch contains approximately 0.1 to 0.2 ounces of loose tea.

* * * * *